United States Patent [19]

Hamill et al.

[11] 4,299,953
[45] Nov. 10, 1981

[54] MYCAROSYLTYLACTONE

[75] Inventors: Robert L. Hamill, Greenwood; Gene M. Wild, Indianapolis, both of Ind.

[73] Assignee: Eli Lilly and Company, Indianapolis, Ind.

[21] Appl. No.: 173,312

[22] Filed: Jul. 29, 1980

[51] Int. Cl.$^3$ .................... C07H 17/08; C07D 313/00
[52] U.S. Cl. ................... 536/17 R; 260/343; 424/181; 424/279; 435/119
[58] Field of Search ................ 536/17 R, 17 C; 260/343

[56] References Cited

U.S. PATENT DOCUMENTS

| | | | |
|---|---|---|---|
| 3,178,341 | 4/1965 | Hamill et al. | 424/121 |
| 3,326,759 | 6/1967 | Hamill et al. | 424/120 |
| 3,344,024 | 9/1967 | Whaley et al. | 424/121 |
| 3,459,853 | 8/1969 | Gorman et al. | 424/121 |
| 4,056,616 | 11/1977 | Reimann et al. | 536/17 R |
| 4,092,473 | 5/1978 | Okamoto et al. | 536/17 |
| 4,161,523 | 7/1979 | Weinstein et al. | 424/181 |
| 4,196,280 | 4/1980 | Umezawa et al. | 536/17 R |
| 4,205,163 | 5/1980 | Mori et al. | 536/17 R |

OTHER PUBLICATIONS

Kinumaki et al., J. Antibiotics, 30 (6), 450–454, 1977, Derwent Abstract.
Yamaguchi et al., J. Antibiotics, 31 (5), 433–440, 1978, Derwent Abstract.
Tsukiura et al., J. Antibiotics, 22 (3), 89–99, 1969.
Suzuki et al., Chemistry Letters, pp. 793–798, 1973.
Nash et al., Am. Society of Microbiology, pp. 462–463, 1980.
Nagel et al., J. Org. Chem., 44 (12), 2050–2052, (1979).
Masamune et al., J. Am. Chem. Soc., 98 (24), 7874–7875, (1976).
Omura et al., Proceedings of 100th Meeting of the Pharmaceutical Society of Japan, 3-10-80.
Grafe et al., (I), J. Antibiotics, 33 (6), 663–664, (1980).
Grafe et al., (II), J. Antibiotics, 33 (6), 574–578, 1980.

Primary Examiner—Henry R. Jiles
Assistant Examiner—Jane T. Fan
Attorney, Agent, or Firm—Nancy J. Harrison; Arthur R. Whale

[57] ABSTRACT

Mycarosyltylactone (5-O-mycarosyl-20-dihydro-20,23-dideoxytylonolide) which has the formula:

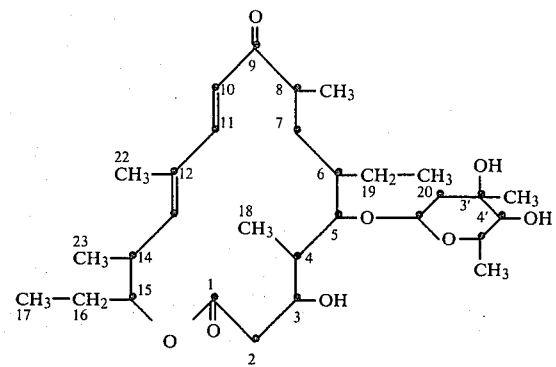

3,4'-diacyl ester derivatives of mycarosyltylactone wherein each of said esters is an ester of a monocarboxylic acid or a hemi-ester of a dicarboxylic acid, each of 1 to 18 carbon atoms, and the corresponding 3-acyl ester derivatives of tylactone, are useful intermediates in the preparation of macrolide antibiotics. New methods for making tylactone and the 3-acyl ester derivatives of tylactone are provided.

14 Claims, 1 Drawing Figure

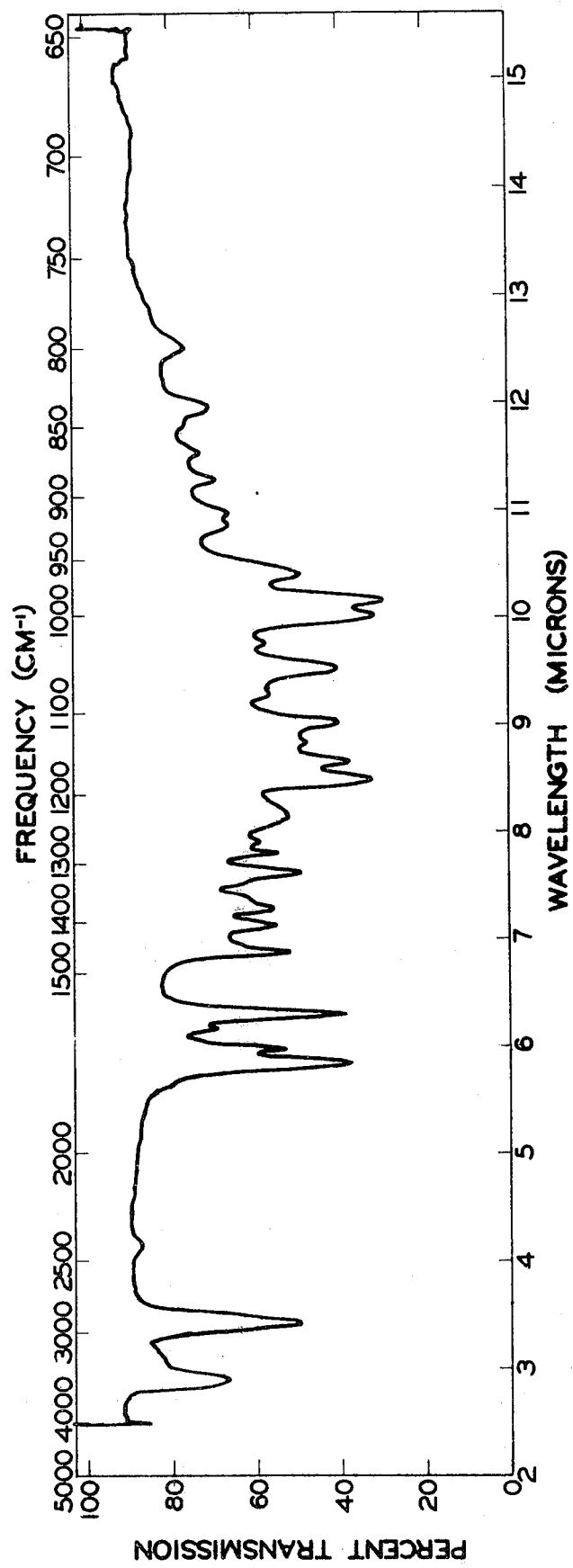

MYCAROSYLTYLACTONE

SUMMARY OF THE INVENTION

This invention relates to a new macrolide compound and to related derivatives from which useful antibiotics, such as tylosin and tylosin derivatives, can be prepared. This new compound, which is 5-O-mycarosyl-20-dihydro-20,23-dideoxytylonolide, will be called mycarosyltylactone for convenience herein. Mycarosyltylactone has structure 1:

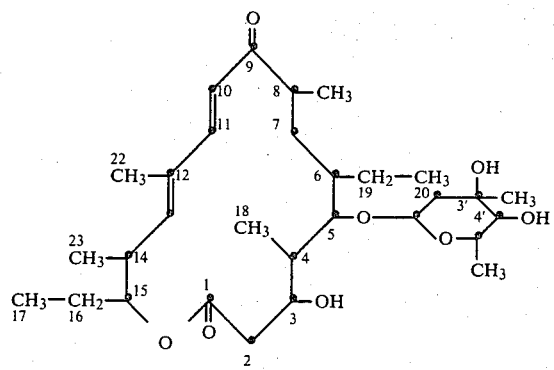

Although no stereochemical assignments are indicated in the structures given hrein, the stereochemistry of the compounds is identical to that of the corresponding portion of tylosin. As the name indicates, the sugar in structure 1 is mycarose.

Related mycarosyltylactone derivatives have structure 2

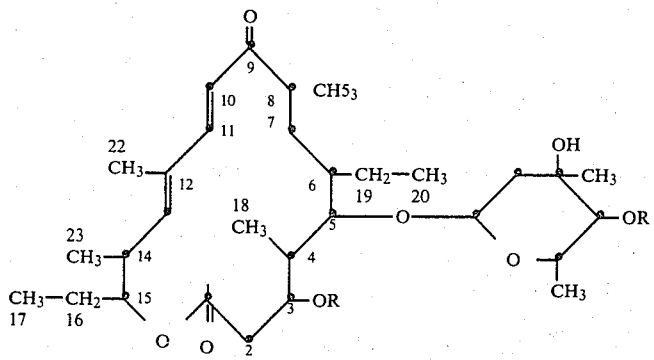

wherein R=an acyl moiety.

This invention further relates to 3-O-acyltylctone derivatives which can be prepared from the mycarosyltylactone derivatives of structure 2. In another aspect, this invention provides a process for preparing tylactone or the 3-O-acyltylactone derivatives by mild acid hydrolysis of mycarosyltylactone or the mycarosyltylactone derivatives of structure 2, respectively.

The 3-O-acyltylactone derivatives of this invention have structure 3:

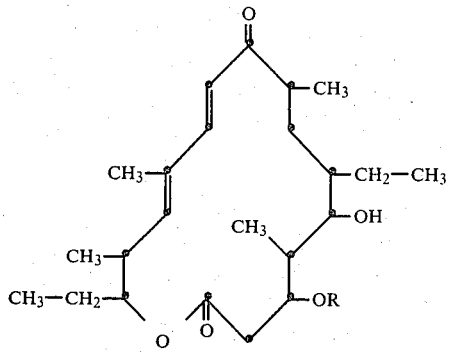

The compounds of structures 1, 2, and 3 are useful intermediates from which 16-membered macrolide antibiotics can be prepared. Thus, for example, this invention provides a new process for chemically derivatizing a compound of formula 3 to give the corresponding 3-monoacyl 16-membered macrolide antibiotic.

DESCRIPTION OF THE DRAWING

The infrared absorption spectrum of mycarosyltylactone in chloroform is presented in the accompanying drawing.

DETAILED DESCRIPTION

The following paragraphs describe the properties of mycarosyltylactone.

Mycarosyltylactone

The structure of mycarosyltylactone is shown in formula 1. Mycarosyltylactone is a white solid which crystallizes from heptane, hexane or ethyl acetatehexane and which melts at about 182°–184° C. It has the following approximate percentage elemental composition: carbon, 67%; hydrogen, 9%; and oxygen, 24%. It has an empirical formula of $C_{30}H_{50}O_8$ and a molecular weight of about 538.

The infrared absorption spectrum of mycarosylatylactone in chloroform is shown in the accompanying drawing. Observable absorption maxima occur at the following frequencies (cm$^-$): 3640 (medium), 2941 and 2907 [doublet (strong)], 2421 (very small), 1712 (strong), 1678 (medium), 1623 (small), 1590 (strong), 1456 (medium), 1404 (small), 1374 (small), 1359 (shoulder), 1314 (small), 1284 (small), 1263 (very small), 1229 (small), 1178 (strong), 1157 (medium), 1134 (very small), 1109 (small), 1078 (very small), 1050 (medium), 1025 (very small), 1000 (strong), 984 (strong), 962 (medium), 920 (very small), 911 (very small), 887 (small), 867 (small), 848 (shoulder), 836 (small), and 799 (small).

The ultraviolet absorption spectrum of mycarosyltylactone in neutral ethanol exhibits an absorption maximum at about 282 nm ($E_{1\ cm}^{1\%} = 568$).

Mycarosyltylactone has the following specific rotation: $[\alpha]_D^{25} -46.4°$ (c 1, $CH_3OH$).

Mycarosyltylactone is nearly insoluble in water, but is soluble in organic solvents such as acetone, methanol, ethanol, dimethylformamide, chloroform, diethyl ether, petroleum ether, benzene and dimethyl sulfoxide.

One important use of mycarosyltylactone is as an intermediate to make tylactone and tylactone derivatives. Tylactone is the subject of a co-pending patent application of Robert L. Hamill, Gerald L. Huff, Richard H. Baltz and Eugene T. Seno, entitled TYLACTONE, Ser. No. 162,976 filed July 2, 1980. A method for making tylactone is the subject of a co-pending patent application of Richard H. Baltz and Eugene T. Seno, entitled PROCESS FOR PREPARING TYLACTONE, Ser. No. 162,977 filed July 2, 1980. The following paragraphs describe the properties of tylactone.

Tylactone

The structure of tylactone is shown in formula 4.

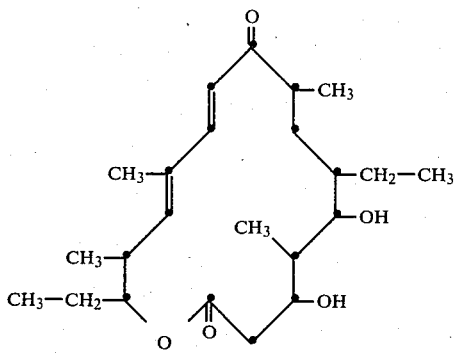

4

Tylactone is a white solid which crystallizes from heptane, hexane or ethyl acetate-hexane and which melts at about 162°–163° C. It has the following approximate percentage elemental composition: carbon, 70%; hydrogen, 9.7%; oxygen, 20.3%. It has an empirical formula of $C_{23}H_{38}O_5$ and a molecular weight of about 394.

The infrared absorption spectrum of tylactone in chloroform has observable absorption maxima at the following frequencies ($cm^{-1}$): 3534 (medium), 2924 (strong), 2398 (weak), 2353 (weak), 1709 (very strong), 1678 (very strong), 1626 (small), 1592 (very strong), 1458 (strong), 1441 (shoulder), 1404 (strong), 1379 (small), 1316 (strong), 1284 (medium), 1181 (very strong), 1143 (strong), 1103 (medium), 1078 (medium), 1049 (very small), 1025 (medium), 984 (very strong), 958 (strong), 923 (medium), 911 (shoulder), 859 (small), 868 (medium), 840 (medium), 820 (very small) and 661 (small).

The ultraviolet (UV) absorption spectrum of tylactone in neutral ethanol exhibits an absorption maximum at about 282 nm ($E_{1\ cm}^{1\%}$ 32 560).

Tylactone has the following specific rotation: $[\alpha]_D^{25} -55.23°$ (c 1, $CH_3OH$).

Electrometric titration of tylactone in 66% aqueous dimethylformamide indicates it has no titratable groups.

Tylactone is nearly insoluble in water, but is soluble in organic solvents such as acetone, methanol, ethanol, dimethylformamide, chloroform, diethyl ether, petroleum ether, benzene and dimethyl sulfoxide.

Chromatography of Mycarosyltylactone

Mycarosyltylactone can be distinguished from tylactone and tylosin by silica-gel thin-layer chromatography (TLC). Sulfuric acid spray, either concentrated or diluted (50%), may be used for detection. With this detection system tylactone appears initially as a yellow-to-brown spot, and mycarosyltylactone appears as a blue-purple spot. If silica-gel plates with a fluorescent background are used in the chromatography, UV detection is convenient. The approximate Rf values of mycarosyltylactone are summarized in Table 1.

TABLE 1

| TLC of Mycarosyltylactone[a] | | |
|---|---|---|
| | Rf Value | |
| Compound | A[b] | B |
| Mycarosyltylactone | 0.17 | 0.44 |
| Tylactone | 0.50 | 0.62 |
| Tylosin | 0.0 | 0.0 |

[a]Medium: Silica gel
[b]Solvent:
A = benzene: ethyl acetate (4:1)
B = benzene: ethyl acetate (3:2)

Preparation of Mycarosyltylactone

Mycarosyltylactone is prepared by culturing a strain of *Streptomyces fradiae* which produces this compound under submerged aerobic conditions in a suitable culture medium until a substantial amount of compound is produced.

The culture medium used to grow the *Streptomyces fradiae* can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of mycarosyltylactone, submerged aerobic fermentation in tanks is preferred. Small quantities of mycarosyltylactone may be obtained by shake-flask culture. Because of the time lag in production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture. The vegetative inoculum is then transferred to a larger tank. The medium used for the vegetative inoculum can be the same as that used for larger fermentations, but other media can also be used.

A preferred method of preparing mycarosyltylactone is that disclosed by Eugene T. Seno and Richard H. Baltz in a co-pending patent application entitled PROCESS FOR PREPARING MYCAROSYLTYLACTONE, Ser. No. 173,313 filed herewith this even date. That method comprises culturing a new microorganism which was obtained by chemical mutagenesis of a *Streptomyces fradiae* strain which produced tylosin. The microorganism obtained by mutagenesis produces only minimal amounts of tylosin, but produces mycarosyltylactone and tylactone as major components.

The new microorganism which produces mycarosylatylactone is classified as a strain of *Streptomyces fradiae*. A culture of this microorganism has been deposited and made part of the stock culture collection of the Northern Regional Research Center, Agricultural Research, North Central Region, 1815 North University Street, Peoria, Illinois, 61604, from which it is available to the public under the accession number NRRL 12201.

As is the case with other organisms, the characteristics of *Streptomyces fradiae* NRRL 12201 are subject to variation. Recombinants, mutants or variants of the NRRL 12201 strain can be obtained by methods known in the art. For example mutants can be obtained by treatment with various known physical and chemical mutagens, such as ultraviolet light, X-rays, gamma rays, and N-methyl-N'-nitro-N-nitrosoguanidine. All natural and induced variants, mutants and recombinants of *Streptomyces fradiae* NRRL 12201 which retain the characteristic of mycarosylatylactone production may be used to prepare the compounds of this invention.

*S. fradiae* NRRL 12201 can be grown at temperatures between about 10° and about 40° C. Optimum production of mycarosyltylactone appears to occur at temperatures of about 28° C.

As is customary in aerobic submerged culture processes, sterile air is bubbled through the culture medium. For efficient antibiotic production the percent of air saturation for tank production should be about 30% or above (at 28° C. and one atmosphere of pressure).

Production of mycarosyltylactone and tylactone can be followed during the fermentation by testing samples of the broth, using TLC or high-performance liquid chromatography with a UV detection system.

Following its production under submerged aerobic fermentation conditions, mycarosyltylactone can be recovered from the fermentation medium by methods used in the art. Because of the limited solubility of mycarosyltylactone in water, it may not be altogether soluble in the medium in which it is produced. Recovery of mycarosyltylactone, therefore, can be accomplished by 1) extraction of the fermentation broth or 2) filtration of the fermentation broth and extraction of both the filtered broth and the mycelial cake. A variety of techniques may be used in the extraction processes. A preferred technique for purification of the filtered broth involves extracting the broth (generally without pH adjustment) with a suitable solvent such as amyl acetate or petroleum ether, concentrating the organic phase under vacuum to give crystals or an oil. The crystals or oil thus obtained may be purified by adsorption chromatography to give mycarosyltylactone and tylactone.

Ester Derivatives

Mycarosyltylactone can be esterified at the 3- and 4'-hydroxyl groups to give the acyl ester derivatives of formula 2 by treatment with acylating agents using methods known in the art. The acyl ester derivatives of mycarosyltylactone are useful as intermediates in the preparation of new macrolide antibiotics.

Typical acylating agents include anhydrides, halides (usually in combination with a base or other acid scavenger) and active esters of organic acids. Acylation can also be achieved by using a mixture of an organic acid and a dehydrating agent such as N,N'-dicyclohexylcarbodiimide.

The derivatives can be prepared by esterification techniques generally known in the art, such as, for example, treatment of the compound with a stoichiometric quantity (or a slight excess) of an acylating agent, such as an acyl anhydride, in an organic solvent (for example, pyridine) at about 0° C. to about room temperature for from about 1 to about 24 hours until esterification is substantially complete. The ester derivative can be isolated from the reaction mixture by standard procedures such as extraction, chromatography and crystallization.

Useful esters are those of organic acids including aliphatic, cycloaliphatic, aryl, aralkyl, heterocyclic carboxylic, sulfonic and alkoxycarbonic acids of from 1 to 18 carbon atoms, and of inorganic acids, such as sulfuric and phosphoric acids.

Preferred esters are those wherein R is an acyl moiety derived from a monocarboxylic acid or dicarboxylic acid of from 1 to 18 carbon atoms.

Representative suitable esters include those derived from acids such as formic, acetic, chloroacetic, propionic, butyric, isovaleric, glucuronic, alkoxycarbonic, stearic, cyclopropanecarboxylic, cyclohexanecarboxylic, β-cyclohexylpropionic, 1-adamantanecarboxylic, benzoic, phenylacetic, phenoxyacetic, mandelic and 2-thienylacetic acids, and alkyl-, aryl-, and aralkyl-sulfonic acids, the aryl- and aralkyl- acids optionally bearing substituents such as halogen, nitro, lower alkoxy and the like on the aromatic moiety. Suitable esters also include hemiesters derived from dicarboxylic acids such as succinic, maleic, fumaric, malonic and phthalic acids.

The compounds of structures 1, 2 and 3 are useful intermediates from which 16-membered macrolide antibiotics can be prepared. For example, mycarosyltylactone (1) can be hydrolyzed using mild acid conditions to give tylactone (4). Likewise, a mycarosyltylactone derivative of formula 2 can be hydrolyzed to give the corresponding 3-O-acyltylactone derivative of formula 3.

Mild acid hydrolysis conditions are known in the art. Appropriate solutions having a pH of about four or below can be used to accomplish the hydrolysis. A polar organic cosolvent, such as an alcohol (for example, ethanol), should be included in the solution to keep the reactants in solution. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating mycarosyltylactone or a 3-O-acylmycarosyltylactone derivative with a mild acid solution for a time sufficient to effect removal of the mycarosyl group to give tylactone, or 3-O-acyltylactone.

Tylactone can be bioconverted to tylosin or tylosin-related compounds as described by Hamill et al. in Ser. No. 162,976. The bioconversion is accomplished by adding tylactone to a growing culture of a bioconverting microorganism. The bioconverting microorganism can be a Streptomyces strain which either produces tylosin itself or is capable of producing tylosin except that it is blocked in tylactone formation.

A strain which is capable of producing tylosin except that it is blocked in tylactone formation can be obtained by treating a tylosin-producing strain with a mutagen and screening survivors for those which are unable to produce tylosin. Those survivors which are unable to produce tylosin are further screened to determine which strains are unable to produce tylactone but are still capable of bioconverting tylactone to tylosin. These strains are identified by adding tylactone to small shake-flask cultures of the selected survivors to determine if they bioconvert tylactone to tylosin.

*Streptomyces fradiae* strains NRRL 2702 and NRRL 2703 are examples of Streptomyces strains which are capable of producing tylosin. A typical mutagen which may be used to obtain the selected strains is N-methyl-N'-nitro-N-nitrosoguanidine.

Tylactone and the 3-O-acyltylactone derivatives are especially useful in the preparation of labeled compounds for biosynthetic or metabolic studies. By labeling either the tylactone portion or the added sugar moieties, specifically labeled tylosin useful for biosynthetic or metabolic studies can be obtained. The acyl moiety of the 3-O-acyltylactone derivatives provides an additional site for labeling.

In order to illustrate more fully the operation of this invention, the following examples are provided:

EXAMPLE 1

A. Shake-flask Fermentation of Mycarosyltylactone

A lyophilized pellet of *Streptomyces fradiae* NRRL 12201 is dispersed in 1-2 ml of sterilized water. A portion of this solution (0.5 ml) is used to inoculate a vegetative medium (150 ml) having the following composition:

| Ingredient | Amount (%) |
| --- | --- |
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12201 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at about 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of Mycarosyltylactone

In order to provide a larger volume of inoculum, 60 ml of vegetative culture, prepared in a manner similar to that described in section A, is used to inoculate 38 L of a second-stage vegetative growth medium having the following composition:

| Ingredient | Amount (%) |
| --- | --- |
| Corn steep liquor | 1.0 |
| Soybean meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |

This second-stage vegetative medium is incubated in a 68-liter tank for about 47 hours at 29° C.

Second-stage culture (4 L) thus prepared is used to inoculate 40 liters of sterile production medium having the following composition:

| Ingredient | Amount (%) |
| --- | --- |
| Fish meal | 0.92 |
| Corn meal | 1.57 |
| Corn gluten | 0.92 |
| CaCO$_3$ | 0.21 |
| NaCl | 0.10 |
| (NH$_4$)$_2$HPO$_4$ | 0.04 |
| Beet molasses | 2.10 |
| Soybean oil (crude) | 3.15 |
| Lecithin | 0.09 |
| Water | 90.90 |

Adjust pH to 7.2 with 50% NaOH solution.

The inoculated production medium is allowed to ferment in a 68-liter tank for about 5 days at a temperature of 28° C. The fermentation medium is aerated with sterile air to keep the dissolved oxygen level between about 30% and 50% and is stirred with conventional agitators at about 300 rpm.

EXAMPLE 2

Isolation of Mycarosyltylactone and Tylactone

Fermentation broth (900 ml), obtained as described in Example 1, Section A, is extracted with petroleum ether (900 ml). The petroleum ether extract is concentrated under an air stream to give an oil. The oil is dissolved in a small amount of ethyl acetate (about 15 ml). Heptane (about 15-20 ml) is added. The ethyl acetate is slowly allowed to evaporate to permit crystallization. The crystals are separated to give 450 mg of a crystalline mixture of tylactone and mycarosyltylactone.

Additional material can be obtained by adding an equal volume of methanol to the remaining whole broth, filtering the resulting solution, and extracting the filtrate with methylene chloride.

The crystalline mixture (400 mg) is separated by dissolving it in benzene. The benzene solution is chromatographed on a silica-gel (Woelm) column, packed in benzene. Elution is monitored by silica-gel thin-layer chromatography, using a benzene:ethyl acetate (3:2) solvent system and conc. sulfuric acid spray for detection. The column is first eluted with benzene to remove lipid substances, then with one liter of benzene:ethyl acetate (9:1), 1400 ml of benzene:ethyl acetate (6:1) and 900 ml of benzene:ethyl acetate (3:1) to separate and isolate tylactone and mycarosyltylactone. Fractions having a volume of about 150 ml are collected. Tylactone is eluted first (fractions 14–19), and mycarosyltylactone is eluted later (fractions 22–26). Fractions containing each are combined, evaporated under vacuum, and crystallized from heptane to give 160 mg of tylactone and 120 mg of mycarosyltylactone.

EXAMPLE 3

3,4'-Di-O-acetyl-5-O-mycarosyltylactone

Mycarosyltylactone (20 mg), prepared as described in Example 2, is dissolved in pyridine (0.5 ml). Acetic anhydride (0.25 ml) is added. The resulting mixture is stirred at room temperature for 15 hours and then is concentrated to dryness under vacuum. The residue is re-evaporated from methanolcyclohexane until a solid is obtained to give 3,4'-di-O-acetyl-5-O-mycarosyltylactone.

EXAMPLES 4–7

3,4'-Di-O-propionyl-5-O-mycarosyltylactone, prepared according to the procedure of Example 3, but using propionic anhydride.

3,4'-Di-O-isovaleryl-5-O-mycarosyltylactone, prepared according to the procedure of Example 3, but using isovaleric anhydride.

3,4'-Di-O-benzoyl-5-O-mycarosyltylactone, prepared according to the procedure of Example 3, but using benzoic anhydride.

3,4'-Di-O-(n-butyryl)-5-O-mycarosyltylactone, prepared according to the procedure of Example 3, but using n-butyric anhydride.

EXAMPLE 8

Preparation of Tylactone from Mycarosyltylactone

Mycarosyltylactone, prepared as described in Example 2, is dissolved in a methanol-aqueous hydrochloric acid solution (pH 1.8). The resulting solution is allowed to stand until hydrolysis is complete (warming over a steam bath for about 30 minutes) and then is adjusted to pH 7.0 by the addition of sodium hydroxide. This solution is extracted with ethyl acetate, dichloromethane or chloroform. The extract is dried and evaporated under vacuum to give tylactone.

EXAMPLE 9

Preparation of 3-O-Acetyltylactone 3,4'-Di-O-Acetyl-5-O-mycarosyltylactone, prepared as described in Example 3, is hydrolyzed according to the method of Example 8 using methanol:0.1 N HCl(1:1; pH 1.5) to give 3-O-acetyltylactone.

EXAMPLE 10–13

3-O-Propionyltylactone, prepared from 3,4'-di-O-propionyl-5-O-mycarosyltylactone of Example 4 according to the procedure of Example 9.

3-O-Isovaleryltylactone, prepared from 3,4'-di-O-isovaleryl-5-O-mycarosyltylactone of Example 5 using the procedure of Example 9.

3-O-Benzoyltylactone, prepared from 3,4'-di-O-benzoyl-5-O-mycarosyltylactone of Example 6, using the procedure of Example 9.

3-O-(n-Butyryl)tylactone, prepared from 3,4'-di-O-(n-butyryl)-5-O-mycarosyltylactone of Example 7, using the procedure of Example 9.

EXAMPLE 14

Preparation of Tylosin from Tylactone

A *Streptomyces fradiae* strain which formerly produced tylosin but which is blocked in macrolide ring closure is fermented according to the procedure described in Example 1, Section A. A temperature of 28° C. is used. Tylactone is added to the fermentation 48 hours after inoculation. The fermentation is then continued until a substantial amount of tylosin is produced, i.e. about three additional days. The presence of tylosin is determined by testing samples of the broth against organisms known to be sensitive to tylosin. One useful assay organism is *Staphylococcus aureus* ATCC 9144. Bioassay is conveniently performed by an automated turbidometric method. Alternative assay methods include thin-layer chromatography and high-performance liquid chromatography with UV detection.

EXAMPLE 15

Preparation of Labeled Tylosin

Mycarosyltylactone is prepared by the method of Examples 1 and 2 except that a labeled acetate, propionate, or butyrate is incorporated into the fermentation medium. Labeled mycarosyltylactone thus produced is used to prepare labeled tylactone using the method of Example 8. The labeled tylactone is used to prepare tylosin according to the procedure of Example 14. Tylosin labeled on the macrolide ring is thereby provided.

EXAMPLE 16

Alternate Preparation of Labeled Tylosin

Tylactone, prepared by the method of Example 8, is used to prepare tylosin according to the method of Example 14 except that a labeled sugar moiety such as glucose is added to the second fermentation to provide tylosin which is labeled on the sugar moieties.

EXAMPLE 17

Preparation of 3-O-Acetyl-5-O-β-desosaminyltylactone

3-O-Acetyltylactone, prepared as described in Example 10, is mixed with 1-α-bromo-2-O-acetyldesosamine hydrobromide (5 equivalents) in the presence of mercuric cyanide in nitromethane (20° C., 10 hours). 3,2'-O-diacetyl-5-O-β-desosaminyltylactone is isolated using silica gel column chromatography. The 2'-acetyl group is removed by allowing this compound to stand in methanol at room temperature to give 3-O-acetyl-5-O-β-desosaminyltylactone (the 3-O-acetyl derivative of antibiotic M-4365 G$_1$).

We claim:

1. Mycarosyltylactone which has the structure:

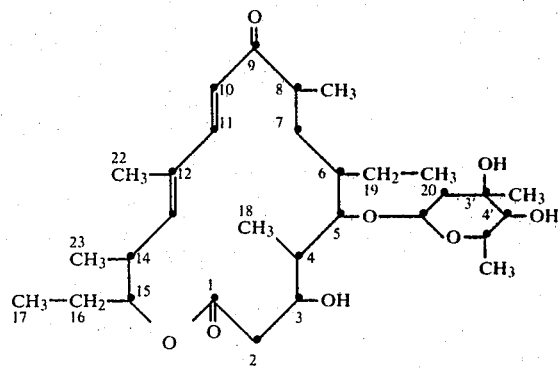

and the 3,4'-diacyl ester derivatives of mycarosyltylactone wherein each of said esters is an ester of a monocarboxylic acid or a hemi-ester of a dicarboxylic acid, each of 1 to 18 carbon atoms.

2. The compound of claim 1 which is mycarosyltylactone.

3. The compounds of claim 1 which are the 3,4'-diacyl ester derivatives of mycarosyltylactone.

4. The compound of claim 3 which is 3,4'-di-O-acetyl-5-O-mycarosyltylactone.

5. The compound of claim 3 which is 3,4'-di-O-propionyl-5-O-mycarosyltylactone.

6. The compound of claim 3 which is 3,4'-di-O-benzoyl-5-O-mycarosyltylactone.

7. The compound of claim 3 which is 3,4'-di-O-isovaleryl-5-O-mycarosyltylactone.

8. The compound of claim 3 which is 3,4'-di-O-(n-butyryl)mycarosyltylactone.

9. 3-O-acyltylactone compounds which have the formula:

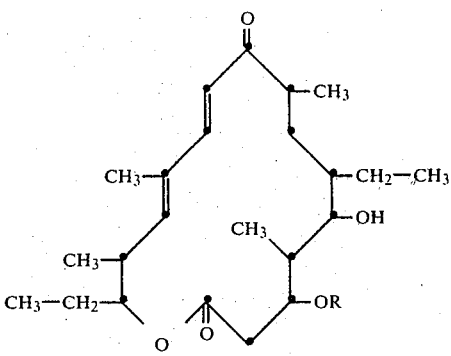

wherein R is an acyl moiety derived from a monocarboxylic acid or dicarboxylic acid of from 1 to 18 carbon atoms.

10. The compound of claim 9 which is 3-O-acetyltylactone.

11. The compound of claim 9 which is 3-O-propionyltylactone.

12. The compound of claim 9 which is 3-O-isovaleryltylactone.

13. The compound of claim 9 which is 3-O-benzoyltylactone.

14. The compound of claim 9 which is 3-(n-butyryl)tylactone.

* * * * *

UNITED STATES PATENT AND TRADEMARK OFFICE
CERTIFICATE OF CORRECTION

PATENT NO. : 4,299,953
DATED : November 10, 1981
INVENTOR(S) : Robert L. Hamill and Gene M. Wild It is certified that error appears in the above-identified patent and that said Letters Patent are hereby corrected as shown below:

Column 1, line 30, "hrein" should read -- herein --; that portion of the second structural formula of column 1 (structure 2) reading " 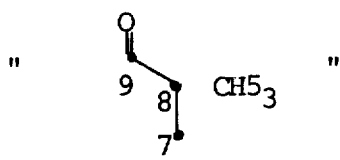 "

should read

-- 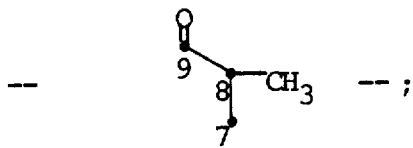 --;

line 60, "acyltylctone" should read -- acyltylactone --.

UNITED STATES PATENT AND TRADEMARK OFFICE
CERTIFICATE OF CORRECTION

PATENT NO. : 4,299,953

DATED : November 19, 1981

INVENTOR(S) : Robert L. Hamill and Gene M. Wild

It is certified that error appears in the above-identified patent and that said Letters Patent are hereby corrected as shown below:

Column 2, line 61, "$(cm^-)$" should read -- $(cm^{-1})$ --.

Column 3, line 64, "$(E_1 \, _{cm}1\%32 \, 560)$" should read -- $(E_1 \, _{cm}1\% = 560)$ --.

Column 8, line 31, add -- Adjust pH to 8.5 with 50% NaOH solution. --.

Signed and Sealed this

Seventh Day of September 1982

[SEAL]

Attest:

Attesting Officer

GERALD J. MOSSINGHOFF

Commissioner of Patents and Trademarks